United States Patent [19]
Bochis

[11] 3,984,549
[45] Oct. 5, 1976

[54] SUBSTITUTED PYRIDO-TRIAZINES AS ANTHELMINTICS

[75] Inventor: Richard J. Bochis, East Brunswick, N.J.

[73] Assignee: Merck & Co., Inc., Rahway, N.J.

[22] Filed: May 28, 1975

[21] Appl. No.: 581,410

[52] U.S. Cl............................ 424/249; 260/248 NS
[51] Int. Cl.².................................. C07D 251/72
[58] Field of Search................ 260/248 NS; 424/249

[56] References Cited
UNITED STATES PATENTS

| | | | |
|---|---|---|---|
| 3,609,148 | 9/1971 | Hoegerle et al. | 260/248 |
| 3,835,145 | 9/1974 | Dickinson et al. | 260/294.8 |

OTHER PUBLICATIONS
Blatter et al., *Tetrahedron Letters*, No. 18, pp. 1087–1091, (1964).

Howard et al., *J. of Organic Chemistry*, vol. 25, pp. 829–832, (1960).
Fairfull et al., *Jour. Chem. Soc.*, pp. 796–802, (1955).

*Primary Examiner*—John M. Ford
*Attorney, Agent, or Firm*—David L. Rose; J. Jerome Behan

[57] ABSTRACT

Pyrido-(1,2-a)-1,3,5-triazines which are variously substituted on the triazine ring at the 3-position and on the pyridine ring on any of the available positions are active anthelmintic and antifungal agents and are prepared by condensing a substituted isocyanate or an isothiocyanate with a pyridyl-isocyanate or isothiocyanate. The compounds are disclosed in compositions and methods for the treatment of helminthiasis and fungal diseases.

9 Claims, No Drawings

SUBSTITUTED PYRIDO-TRIAZINES AS ANTHELMINTICS

SUMMARY OF THE INVENTION

This invention relates to novel organic chemical compounds which are effective against helminthiasis and fungi. Specifically this invention relates to novel pyrido-(1,2-a)-1,3,5-triazines which are variously substituted on the pyridine and triazine rings. Thus, it is an object of this invention to provide for novel compounds. It is a further object of this invention to provide for substituted novel pyrido-(1,2-a)-1,3,5-triazines. A still further object of this invention is to provide for processes for the preparation of the compounds of this invention. Another object is to provide for compositions and methods which utilize the compounds of this invention for the treatment of helminthiasis and fungi. Further objects will become apparent from the following Description of the Invention.

DESCRIPTION OF THE INVENTION

The novel pyrido-(1,2-a)-1,3,5-triazines of this invention are set forth in the following structural formula:

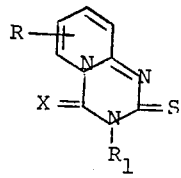

wherein X is oxygen or sulfur; R is hydrogen, loweralkyl, loweralkoxy, halogen or phenyl; and $R_1$ is phenyl, halophenyl, alkyl of from 1 to 10 carbon atoms, pyridyl or substituted pyridyl, wherein the substituents are halogen, loweralkyl, loweralkoxy, phenyl or nitro provided that when R is hydrogen, said pyridyl must be substituted.

In the instant description of this invention the term "loweralkyl" is deemed to include those alkyl groups containing from 1 to 6 carbon atoms which may be arranged in either a straight or branched configuration. Exemplary of such loweralkyl groups are methyl, ethyl, propyl, butyl, amyl, hexyl, isopropyl, tert butyl and the like.

The term "loweralkoxy" is deemed to include those alkoxy groups containing from 1 to 6 carbon atoms which may be arranged in either a straight or branched configuration. Exemplary of such loweralkoxy groups are methoxy, ethoxy, propoxy, isopropoxy, sec butoxy, amyloxy, hexoxy and the like.

The term "halogen" is deemed to include the halogen atoms, fluorine, chlorine, bromine and iodine.

Specific preferred embodiments of the instant invention are:

7-chloro-3-(5-chloro-2-pyridyl)-pyrido-(1,2-a)-1,3,5-triazine-2,4-dithione 3-(2-pyridyl)-pyrido-(1,2-a)-1,3,5-triazine-2,4-dithione 8-methyl-3-(3-methyl-2-pyridyl)-pyrido-(1,2-a)-1,3,5-triazine-2,4-dithione 9-chloro-3-(3-chloro-2-pyridyl)-pyrido-1,2-a)-1,3,5-triazine-2,4-dithione The compounds of this invention are active anthelmintic and antifungal agents. The disease or group of diseases described generally as helminthiasis is due to infestation of the animal body with parasitic worms known as helminths. Helminthiasis is a prevalent and serious economic problem in domesticated animals such as swine, sheep, cattle, goats, dogs and poultry. Among the helminths, the group of worms described as nematodes causes widespread and often times serious infection in various species of animals. The most common genera of nematodes infecting the animals referred to above are *Haemonchus, Trichostrongylus, Ostertagia, Nematodirus, Cooperia, Bunostomum, Oesophagostomum, Chabertia, Trichuris* (whipworm) *Ascaris, Capillaria, Heterakis* and *Ancylostoma*. The parasitic infections known as helminthiasis lead to anemia, malnutrition, weakness, weight loss, severe damage to the walls of the intestinal tract and, if left untreated, often results in death of the infected animals. When used as anthelmintic agents, they may be administered orally in a unit dosage form such as a capsule, bolus, tablet or as a liquid drench.

The drench is normally an aqueous suspension, or dispersion of the active ingredient together with a suspending agent and a wetting agent or like excipient. Preferred drench formulations generally contain from about 5 to 50% by weight of the pyridyl triazines of this invention. The tablets, capsules and boluses comprise the active ingredient admixed with a carrier vehicle such as starch, talc, magnesium stearate and the like. Such unit dosage formulations may be varied widely with respect to their total weight and content of anthelmintic agent depending upon factors such as the type of host animal to be treated, the severity and type of the infection and the weight of the host. Generally such formulations may contain from 5 to 95% by weight of the active ingredient.

The pyrido triazines of this invention may also be added to the normal daily feed or water ration of the animal being treated. It may be dispersed in the feed or used as a top dressing, or in the form of pellets which are then added to the finished feed. When used in the animals water the compounds are suspended therein using appropriate suspending agents. Top dressings for feed or finished medicated feed or water generally contains from 0.1 to 5% by weight of the active ingredient. However, it is preferred to utilize an intermediate feed or water additive in a concentrate in which the active compounds are uniformly admixed with nutritionally acceptable inert ingredients to the extent of about 5 to 50% by weight. These concentrates are than added to the animals feed to provide for a finished feed or water of the concentration set forth above.

Examples of such concentrates are as follows:

| | | |
|---|---|---|
| A. | 7-Chloro-3-(5-chloro-2-pyridyl) pyrido-(1,2-a) 1,3,5-triazine-2,4-dithione | 20 lbs. |
| | Corn distillers dried grains | 80 lbs. |
| B. | 3-(2-Pyridyl)-pyrido-(1,2-a)-1,3,5-triazine-2,4-dithione | 35 lbs. |
| | Wheat Shorts | 65 lbs. |

The particular amount of active compounds depends upon a variety of factors such as size and health of the host animal and the type of helminth, however, generally satisfactory results are obtained when from about 5 to 125 mg. per kg. of animal body weight are administered. Such administration may be in a single daily dose or in a series of divided doses. Generally satisfactory results are obtained when from about 10 to 75 mg. per kg. of animal body weight is administered.

The pyrido (1,2-a)-1,3,5-triazines of this invention are prepared by condensing an appropriately substituted isocyanate or isothiocyanate with an appropriately substituted pyridyl isothiocyanate according to the following reaction scheme:

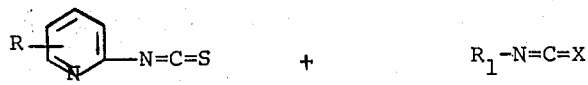

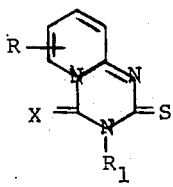

wherein X, R and $R_1$ are as previously defined.

The reactants are combined in an inert solvent or are combined without any solvent and stirred at from room temperature to 100° C. for about ½ hour to 10 days. Generally, however, the reaction is complete in from about 1 to 24 hours at room temperature. Following the reaction period the product pyrido (1,2-a)-1,3,5-triazine is isolated by techniques known to those skilled in this art.

As will be realized to those skilled in this art when X is sulfur, $R_1$ is pyridyl and the substituent on said pyridyl group is the same as the R group, the reaction is actually a dimerization of a pyridyl isothiocyanate. Depending on the particular substituent on the pyridyl isothiocyanate this dimerization can occur at varying rates. The unsubstituted pyridyl isothiocyanate can on standing at room temperature for just a few hours have a significant amount of dimer present therein. This propensity of the pyridyl isothiocyanate to spontaneously dimerize is beneficial when such dimerization is the desired reaction. However, when it is desired to react the pyridyl isothiocyanate with another isothiocyanate or with an isocyanate, this dimerization is a hindrance to achieving the desired reaction product. This may be circumvented by heating the pyridyl isothiocyanate which is contaminated with dimer or heating the pure dimer itself to a point at which the dimer is broken down into two molecules of the monomer, pyridyl isothiocyanate and reacting the monomer immediately, preferably in situ, with the other isothiocyanate or isocyanate reactant. Generally heating the dimer to a temperature of about 80° C. will decouple the dimer and make it available for reaction with the other reactant. It is preferable, but not necessary to utilize an excess of the second reactant for reaction with the pyridylisothiocyanate in order to avoid redimerization prior to the desired reaction.

The solvents preferred for the above reactions are aprotic solvents such as acetonitrile, ether, tetrahydrofuran and the like. The decoupling reaction is run usually at the reflux temperature of the solvent employed, up to about 80° C. and is complete generally in from ½ to 3 hours. The coupling reaction is usually run at about room temperature as above stated.

The starting materials for this process, the pyridyl isothiocyanates and the other reacting isothiocyanates or isocyanates, are generally known in this art or are readily prepared by procedures well known in this art. Generally such starting materials are prepared from the corresponding amine and thiophosgene or phosgene. They are isolated by techniques well known to those skilled in this art.

The following examples are provided in order that the instant invention may be more fully understood. They are not intended to be limitative of this invention.

EXAMPLE 1

7-Chloro-3-(5-chloro-2-pyridyl) pyrido-(1,2-a) 1,3,5-triazine-2,4-dithione

5-Chloro-2-pyridylisothiocyanate

A solution of 16.3 ml. of thiophosgene in 600 ml. of ether is added with rapid stirring to a suspension of 25.6 g. of 5-chloro-2-aminopyridine and 42 g. of calcium carbonate in 600 ml. of water. The reaction mixture is stirred for 1½ hours and the ether layer separated and the water layer extracted with a 400 ml. portion of ether. The combined ether extracts are washed with water, dried over magnesium sulfate and evaporated to dryness in vacuo affording 29.9 g. of a dark red oil. The oil is distilled at 0.75 mm. of Hg. at a temperature 96° C. affording 5-chloro-2-pyridylisothiocyanate.

B. 7-Chloro-3-(5-chloro-2-pyridyl) pyrido-(1,2-a) 1,3,5-triazine-2,4-dithione 1.1 G. of freshly distilled 5-chloro-2-pyridyl isothiocyanate is dissolved in 5 ml. acetonitrile and allowed to stand at room temperature for 3 days. The reaction mixture is filtered and the solid material washed with acetonitrile affording 7-chloro-3-(5-chloro-2-pyridyl) pyrido-(1,2-a) 1,3,5-triazine-2,4-dithione m.p. 131°–132° C.

EXAMPLE 2

3-(2-pyridyl) pyrido (1,2-a) 1,3,5-triazine-2,4-dithione

A. Pyridyl 2-isothiocyanate

A suspension of 56.4 g. of 2-aminopyridine and 126 g. of calcium carbonate in 1800 ml. of water is added to a solution of 73.5 g. of thiophosgene in 1800 ml. of ether. The reaction mixture is stirred at room temperature for 75 minutes, the ether layer is separated and the water layer extracted with ether. The combined ether extracts are dried and evaporated to dryness in vacuo. The liquid residue is fractionally distilled with the fraction boiling at 72° C. at 0.35 mm. of Hg. providing pyridyl-2-isothiocyanate.

B. 3-(2-pyridyl) pyrido (1,2-a) 1,3,5-triazine-2-4-dithione

10 G. of freshly distilled 2-pyridylisothiocyanate is dissolved in 100 ml. of acetonitrile and the reaction mixture stirred at room temperature for 2 days. The solid precipitate is filtered and washed with fresh acetonitrile affording 3-(2-pyridyl) pyrido (1,2-a) 1,3,5-triazine-2,4-dithione m.p. 107°–109° C.

EXAMPLE 3

9-Methyl-3-(3-methyl-2-pyridyl) pyrido (1,2-a) 1,3,5-triazine-2,4-dithione

Following the procedure of Examples 1A and 2A, 21.6 g. of 2-amino-3-methylpyridine, 42 g. of calcium carbonate and 24.5 g. of thiophosgene are converted into 3-methyl-2-pyridylisothiocyanate with a b.p. of 84° C. at 0.5 mm. of Hg. 10 G. of the freshly distilled isothiocyanate is dissolved in 100 ml. of acetonitrile and the reaction mixture carried out as in Examples 1B and 2B affording 9-methyl-3-(3-methyl-2-pyridyl) pyrido (1,2-a) 1,3,5-triazine-2,4-dithione m.p. 131°–132° C.

EXAMPLE 4

7-Bromo-3-(5-bromo-2-pyridyl) pyrido(1,2-a) 1,3,5-triazine 2,4-dithione

Following the procedures of Examples 1 and 2, 25.4 g. of 5-bromo-2-aminopyridine, 31 g. of calcium carbonate and 18.1 g. of thiophosgene is converted to 5-bromo-2-pyridylisothiocyanate with a b.p. of 105° C. at 0.5 mm. of Hg. 5 G. of the above freshly distilled isothiocyanate is dissolved in 50 ml. of acetonitrile and allowed to stand overnight at room temperature. The reaction mixture is filtered and the solid material washed with acetonitrile affording 7-bromo-3-(5-bromo-2-pyridyl) pyrido(1,2-a) 1,3,5-triazine 2,4-dithione m.p. 77° C.

EXAMPLE 5

9-Phenyl-3-(3-phenyl-2-pyridyl) pyrido(1,2-a) 1,3,5-triazine-2,4-dithione

6 G. of 2-amino-3-phenylpyridine and 7.4 g. of calcium carbonate in 500 ml. of water is added to a solution of 2.9 ml. thiophosgene in 105 ml. of ether. The reaction mixture is stirred at room temperature for 3 hours and the ether layer is separated. The water layer is extracted with ether and the combined ether extracts dried and evaporated to dryness affording 3-phenyl-2-pyridylisothiocyanate. The residue from the evaporation is allowed to stand at room temperature for 3 days. The reaction mixture is then triturated with ether and filtered affording 9-phenyl-3-(3-phenyl-2-pyridyl) pyrido (1,2-a) 1,3,5-triazine-2,4-dithione m.p. 90°–92° C.

EXAMPLE 6

9-Chloro-3-(3-chloro-2-pyridyl) pyrido (1,2-a) 1,3,5-triazine-2,4-dithione

Following the procedure of Example 5, 6.4 g. of 2-amino-3-chloropyridine, 11 g. of calcium carbonate and 6.3 g. of thiophosgene is converted into 3-chloro-2-pyridylisothiocyanate b.p. 86° C. at 0.25 mm. of Hg. Upon standing overnight, the freshly distilled 3-chloro-2-pyridylisothiocyanate solidifies affording 9-chloro-3-(3-chloro-2-pyridyl) pyrido (1,2-a) 1,3,5-triazine-2,4-dithione m.p. 120°–122° C.

EXAMPLE 7

7-Methoxy-3-(5-methoxy-2-pyridyl) pyrido (1,2-a) 1,3,5-triazine-2,4-dithione

A. 2-Amino-5-methoxypyridine is prepared by combining 55 g. of 2-amino-5-iodopyridine, 20 g. of sodium methoxide, 5 g. of copper powder, 500 ml. of methanol in a glass lined bomb and rocking at 150° C. for 12 hours. Upon concentration to dryness, an extraction with chloroform extracts are dried and evaporated to dryness in vacuo. The residue is chromatographed on 1200 g. of silica gel eluting with 50% ethylacetate and methylenechloride affording 2-amino-5-methoxy pyridine.

10 G. of 2-amino-5-methoxy pyridine and 17.8 g. of calcium carbonate in 275 ml. of water is added to a solution of 10:1 g. of thiophosgene in 275 ml. of ether. The reaction mixture is stirred at room temperature for 3½ hours and the layers separated and the aqueous layer extracted with ether. The combined ether extracts are washed with sodium chloride, dried and evaporated to dryness in vacuo. The residue is fractionally distilled at 105° C. at 0.5 mm. of Hg. affording 5-methoxypyridine-2-isothiocyanate.

C. The distillate from Step B is stirred into 25 ml. of acetonitrile and the reaction mixture is stirred overnight at room temperature. The reaction mixture is filtered and the residue washed with acetonitrile affording 3.3 g. of 7-methoxy-3-(5-methoxy-2-pyridyl) pyrido (1,2-a) 1,3,5-triazine-2,4-dithione m.p. 124°–126° C.

EXAMPLE 8

3-Methyl pyrido (1,2-a) 1,3,5-triazine-2-one-4-thione

275 Mg. of the dimer of pyridyl-2-isothiocyanate (prepared in Example 2:3-(2-pyridyl) pyrido (1,2-a) 1,3,5-triazine-2,4-dithione) is heated at 70° C. for 1 hour along with 5 ml. of dimethyl formamide and 390 mg. of methyl isocyanate. A precipitate forms after 45 minutes of heating. The reaction mixture is allowed to cool with stirring. The solid material is filtered, washed with ether and dried in vacuo overnight affording 280 mg. of 3-methyl pyrido (1,2-a) 1,3,5-triazine-2-one-4-thione m.p. 262°–264° C. (dec.)

EXAMPLE 9

3-(4-Chlorophenyl) pyrido (1,2-a) 1,3,5-triazine-2-one-4-thione

544 Mg. of 3-(2-pyridyl) pyrido (1,2-a) 1,3,5-triazine-2,4-dithione is combined with p-chloro phenylisocyanate and 10 ml. of acetonitrile. The reaction mixture is heated at 70° C. for 1 hour with a precipitate appearing after ½ hour. The reaction mixture is allowed to cool to room temperature with stirring. The solid material is filtered, washed twice with acetone, once with ether and dried in vacuo affording 3-(4-chlorophenyl) pyrido (1,2-a) 1,3,5-triazine-2-one-4-thione m.p. 209°–212° C.

EXAMPLE 10

8-Chloro 3-(n-decyl) pyrido (1,2-a) 1,3,5-triazine-2,4-dithione 0.511 G. of 4-Chloro-2-pyridyl isothiocyanate and 1.8 g. of n-decylisothiocyanate are combined and heated at 85° C. for 20 hours. The temperature is lowered to 75° C. and continued for 8 days. The reaction mixture is cooled, triturated with ether, filtered, washed with water and dried affording 8-chloro 3-(n-decyl) pyrido (1,2-a) 1,3,5-triazine-2,4-dithione m.p. 153°–155° C.

What is claimed is:

1. A pyrido (1,2-a) 1,3,5-triazine having the formula:

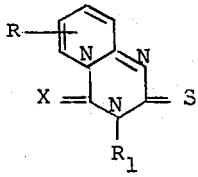

wherein
X is oxygen or sulfur;
R is hydrogen, loweralkyl, loweralkoxy, halogen or phenyl; and
$R_1$ is phenyl, halophenyl, alkyl of from 1 to 10 carbon atoms, pyridyl or substituted pyridyl wherein the substituents are halogen, loweralkyl, loweralkoxy, phenyl or nitro provided that when R is hydrogen, said pyridyl must be substituted.

2. The compound of claim 1 in which X is sulfur.

3. The compound of claim 1 wherein $R_1$ is pyridyl or substituted pyridyl wherein the substituents are halogen, loweralkyl, loweralkoxy, phenyl or nitro.

4. The compound of claim 3 which is 7-chloro-3-(5-chloro-2-pyridyl)-pyrido-(1,2-a)-1,3,5-triazine-2,4-dithione.

5. The compound of claim 3 which is 3-(2-pyridyl)-pyrido-(1,2-a)-1,3,5-triazine 2,4-dithione.

6. The compound of claim 3 which is 8-methyl-3-(3-methyl-2-pyridyl)-pyrido (1,2-a)-1,3,5-triazine-2,4-dithione.

7. The compound of claim 3 which is 9-chloro-3-(3-chloro-2-pyridyl)-pyrido-(1,2-a)-1,3,5-triazine-2,4-dithione.

8. A composition useful for the treatment of helmithiasis in animals which comprises an inert carrier and from 0.01 to 95% by weight of a compound having the formula:

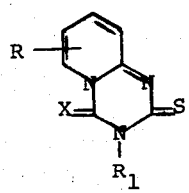

wherein
X is oxygen or sulfur;
R is hydrogen, loweralkyl, loweralkoxy, halogen or phenyl; and
$R_1$ is phenyl, halophenyl, alkyl of from 1 to 10 carbon atoms, pyridyl or substituted pyridyl wherein the substituents are halogen, loweralkyl, loweralkoxy, phenyl or nitro.

9. A method for treating helminthiasis which comprises administering to an animal infected with helminthiasis an effective amount of a compound having the formula:

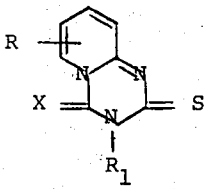

wherein
X is oxygen or sulfur;
R is hydrogen, loweralkyl, loweralkoxy, halogen or phenyl; and
$R_1$ is phenyl, halophenyl, alkyl of from 1 to 10 carbon atoms, pyridyl or substituted pyridyl wherein the substituents are halogen, loweralkyl, loweralkoxy, phenyl or nitro.

* * * * *